(12) United States Patent
Freeman

(10) Patent No.: US 9,867,976 B2
(45) Date of Patent: Jan. 16, 2018

(54) LONG-TERM WEAR ELECTRODE

(71) Applicant: ZOLL Medical Corporation, Chelmsford, MA (US)

(72) Inventor: Gary A. Freeman, Waltham, MA (US)

(73) Assignee: ZOLL MEDICAL CORPORATION, Chelmsford, MA (US)

( * ) Notice: Subject to any disclaimer, the term of this patent is extended or adjusted under 35 U.S.C. 154(b) by 0 days.

(21) Appl. No.: 15/060,694

(22) Filed: Mar. 4, 2016

(65) Prior Publication Data

US 2016/0256676 A1 Sep. 8, 2016

Related U.S. Application Data

(60) Provisional application No. 62/129,204, filed on Mar. 6, 2015.

(51) Int. Cl.
| | | |
|---|---|---|
| A61N 1/00 | (2006.01) |
| A61N 1/04 | (2006.01) |
| A61N 1/36 | (2006.01) |
| A61N 1/362 | (2006.01) |
| A61N 1/39 | (2006.01) |

(52) U.S. Cl.
CPC ........... *A61N 1/046* (2013.01); *A61N 1/0456* (2013.01); *A61N 1/0472* (2013.01); *A61N 1/0492* (2013.01); *A61N 1/0496* (2013.01); *A61N 1/36014* (2013.01); *A61N 1/3625* (2013.01); *A61N 1/39* (2013.01)

(58) Field of Classification Search
CPC .... A61N 1/046; A61N 1/0472; A61N 1/0492; A61N 1/0496; A61N 1/36014; A61N 1/39
See application file for complete search history.

(56) References Cited

U.S. PATENT DOCUMENTS

| 4,833,179 A | 5/1989 | Young et al. |
| 4,952,650 A | 8/1990 | Young et al. |
| 5,670,557 A | 9/1997 | Dietz et al. |
| 6,148,233 A | 11/2000 | Owen et al. |

(Continued)

FOREIGN PATENT DOCUMENTS

| WO | 2013181508 A1 | 12/2013 |
| WO | 2014160848 A1 | 10/2014 |

OTHER PUBLICATIONS

"3M™ Electrically Conductive Cushioning Gasket Tape ECG-8035/ECG-8055/ECG-8075", Technical Data, Feb. 2010.
(Continued)

*Primary Examiner* — Robert N Wieland
(74) *Attorney, Agent, or Firm* — The Webb Law Firm

(57) ABSTRACT

An electrode for use with a therapeutic current delivery system can include a flexible, water vapor-permeable, conductive adhesive material; a current dispersing element in contact with the conductive adhesive material; and a non-conductive, flexible, water vapor-permeable, electrically-insulating top layer provided in contact with the current dispersing element. The current dispersing element can be conductive at least laterally along a plane of the electrode. The conductive adhesive material can be conductive in a direction substantially orthogonal to the plane of the electrode and semi-conductive in a direction substantially lateral to the plane of the electrode.

36 Claims, 13 Drawing Sheets

(56) References Cited

U.S. PATENT DOCUMENTS

| | | | |
|---|---|---|---|
| 6,548,727 | B1 | 4/2003 | Swenson |
| 7,110,163 | B2 * | 9/2006 | Webber .............. G02F 1/133305 |
| | | | 359/295 |
| 9,162,045 | B2 | 10/2015 | Jones |
| 2002/0072664 | A1 | 6/2002 | Katzenmaier et al. |
| 2003/0004558 | A1 | 1/2003 | Gadsby |
| 2003/0055478 | A1 * | 3/2003 | Lyster .................... A61N 1/046 |
| | | | 607/142 |
| 2007/0238944 | A1 | 10/2007 | Axelgaard |
| 2008/0215128 | A1 | 9/2008 | Rainey et al. |
| 2013/0324868 | A1 | 12/2013 | Kaib et al. |
| 2013/0325096 | A1 | 12/2013 | Dupelle et al. |
| 2014/0303680 | A1 | 10/2014 | Donnelly et al. |

OTHER PUBLICATIONS

3M "XYZ-Axis Electrically Conductive Tape 9712", Technical Data, Aug. 2001.

ASTM D1388-14, "Standard Test Method for Stiffness of Fabrics", Designation: D1388-14, Copyright ASTM International, West Conshohocken, PA, US.

ASTM E-96-80, "Standard Test Methods for Water Vaport Transmission of Materials", Designation: E96/E96M—14, Copyright ASTM International, West Conshohocken, PA, US—corresponds to ASTM E-96-80 (Version E96/E96M-13).

Clough et al., "Innovations in ePTFE Fiber Technology: New Capabilities, New Applications, New Opportunities", W.L. Gore & Assocs. Inc., (2007).

"EPTFE Fiber Solutions," Technical Bulletin of W.L. Gore & Assocs. Inc., (2009).

Khil et al., "Electrospun Nanofibrous Polyurethane Membrane as Wound Dressing", Journal of Biomedical Materials Research Part B: Applied Biomaterials, 2003, pp. 675-679, vol. 62, No. 2.

Sancaktar et al., "Electrically Conductive Epoxy Adhesives", Polymers, 2011, pp. 427-466, vol. 3.

Slaten et al., "Comparison of Elected Properties of Barrier Textile Materials Used in Durable, Moisture Repellant Protective Clothing," J. Testingard Evaluation, JTEVA, (Nov. 1994), pp. 577-580, vol. 22, No. 6.

"Water Resistance: Hydrostatic Pressure Test," AATCC Test Method 127-2014, (2014).

* cited by examiner

METHOD 1

METHOD 2 ate cardiac pacing (TCP).

LONG-TERM WEAR ELECTRODE

CROSS REFERENCE TO RELATED APPLICATIONS

This application claims priority to U.S. Provisional Patent Application No. 62/129,204 entitled "Long-Term Wear Electrode", filed Mar. 6, 2015, the disclosure of which is hereby incorporated in its entirety by reference.

BACKGROUND OF THE DISCLOSURE

Field of the Disclosure

The present disclosure is directed to a wearable electrode for the delivery of therapeutic electrical current, using such an electrode, where the electrode is both breathable and waterproof, and with the conductive properties to be able to support the efficacious delivery of high current electrical therapy.

Description of Related Art

Cardiac arrhythmias, such as ventricular fibrillation and ventricular tachycardia, are electrical malfunctions of the heart, in which regular electrical impulses in the heart are replaced by irregular, rapid impulses. These irregular, rapid impulses can cause the heart to stop normal contractions, thereby interrupting blood flow therethrough. Such an interruption in blood flow can cause organ damage or even death.

Normal heart contractions, and thus normal blood flow, can be restored to a patient through application of electric shock. This procedure, which is called defibrillation, has proven highly effective at treating patients with cardiac arrhythmias, provided that it is administered within minutes of the arrhythmia. Portable, wearable defibrillator systems have been developed which monitor a patient's cardiac activity, detect arrhythmias, and provide defibrillation electric shocks to restore normal heart contractions and blood flow.

Various other pathophysiological conditions may also be treated by the delivery of therapeutic electrical current to physiologic tissues such as the myocardium, nerves, or skeletal muscles using such methods as transthoracic cardiac pacing (TCP).

In the current state of the art, a so-called "dry" therapeutic electrode may be employed where the conductive gel is stored and then deployed via electronically-activated gas pressure, much like an air-bag in a car, such as is manufactured by ZOLL Medical Corporation, Pittsburgh Pa. In this case, separate electrocardiogram (ECG) monitoring electrodes are used.

Alternatively, self-adhesive electrodes such as are used on conventional, non-wearable defibrillators may be employed. In this case, the electrodes are capable of performing both the functions of ECG monitoring and defibrillation. The self-adhesive defibrillator electrodes of these systems can be large, e.g., 2-8 inches in diameter, and use vapor impermeable materials such as metal foils, hydrophilic, water saturated conductive hydrogels, and electrically insulating layers that prevent the patient's expired vapor from the skin surface from evaporating, eventually softening the epidermis and resulting in degradation of the structural integrity of the skin leading to sloughing and peeling of the skin when the electrode is removed after extended wear. As a result, the patient's skin may become irritated which can lead to the patient being non-compliant with his/her treatment when he/she refuses to or can no longer wear the electrodes.

Also, the materials from which these electrodes are made and the adhesives that are used are not waterproof during bathing or showering and do not conform well to the patient's body or movement. This results in the electrodes having to be replaced frequently, often on a daily basis.

Thus, there is a need for an electrode that is less irritating to the patient's skin that remains adhered to the patient's skin for a longer time period, for example, as long as two weeks. A vapor permeable self-adhesive wearable electrical therapy electrode would be desirable over the current art for reducing thickness and weight while at the same time increasing patient comfort and increasing the duration of continuous electrode wear.

SUMMARY OF THE DISCLOSURE

An electrode for use with a therapeutic current delivery system can comprise: a flexible, water vapor-permeable, conductive adhesive material; a current dispersing element in contact with the conductive adhesive material; and a non-conductive, flexible, water vapor-permeable, electrically-insulating top layer provided in contact with the current dispersing element. The current dispersing element can be conductive at least laterally along a plane of the electrode. The conductive adhesive material can be conductive in a direction substantially orthogonal to the plane of the electrode and semi-conductive in a direction substantially lateral to the plane of the electrode.

In one example, the current dispersing element can be conductive in a direction orthogonal to the plane of the electrode. The water vapor permeability of the electrode can be greater than 100 gm/m$^2$/24 hours. In one example, the therapeutic current delivery system can be a defibrillation system or a pacing system. In an example, the electrode can be configured to deliver a defibrillation pulse. The defibrillation pulse can comprise a therapeutic pulse having an energy of at least 200 joules. In another example, the electrode can be configured to deliver at least one pacing pulse. The pacing pulse can comprise a current pulse having a duration in a range of 10-40 ms and an amplitude of at least 50 mAmps. The electrode can be configured to uniformly distribute current to a patient.

In one example, the flexible, water vapor-permeable, conductive adhesive material can comprise a material selected from the group consisting of an electro-spun polyurethane adhesive, a polymerized microemulsion pressure sensitive adhesive, an organic conductive polymer, an organic semi-conductive conductive polymer, an organic conductive compound and a semi-conductive conductive compound, and combinations thereof. In another example, the flexible, water vapor-permeable, conductive adhesive layer can comprise a material selected from the group consisting of poly(3,4-ethylene dioxitiophene), doped with poly(styrene sulfonate), (PEDOT:PSS) poly(aniline) (PANI), poly(thiopene)s, and poly(9,9-dioctylfluorene co-bithiophen) (F8T2), and combinations thereof. In an example, a thickness of the flexible, water vapor-permeable, conductive adhesive material can be between 0.25 and 50 mils. In another example, the water vapor-permeable, conductive adhesive material can comprise conductive particles.

In one example, the current dispersing element can comprise a metallic wire mesh. The metallic wire mesh can comprise a metal selected from the group consisting of copper, tin, nickel, silver, gold, and combinations thereof. In another example, the conductive, current dispersing element can comprise nickel-plated carbon-filled fibers. In one example, the current dispersing element can be segmented.

In an example, a backing can be attached to the flexible, water vapor-permeable, conductive adhesive material. The backing can extend beyond an outer surface of the electrode. In one example, a frame can be provided on an outer surface of the non-conductive, flexible, water vapor-permeable, electrically-insulating top layer. The frame can be disposed around the perimeter of the electrode.

In one example, a therapeutic current delivery system can comprise: a therapeutic current delivery device; at least one cable connector connected to the therapeutic current delivery device; and at least one electrode connected to the at least one cable connector. The at least one electrode can comprise: a flexible, water vapor-permeable, conductive adhesive material; a current dispersing element in contact with the conductive adhesive material; and a non-conductive, flexible, water vapor-permeable, electrically-insulating top layer provided in contact with the current dispersing element. The current dispersing element can be conductive at least laterally along a plane of the electrode. The conductive adhesive material can be conductive in a direction substantially orthogonal to the plane of the electrode and semi-conductive in a direction substantially lateral to the plane of the electrode. In one example, the cable connectors can be no more than 10 inches long. In another example, the therapeutic current delivery device can be a defibrillation device, a pacing device, or a nerve stimulation device.

In another example, an electrode for use with a therapeutic current delivery system can comprise: a flexible, water vapor-permeable, conductive adhesive material; a current dispersing element in contact with the conductive adhesive material to receive a therapeutic current from a connector and distribute the therapeutic current over a plane of the electrode; and a non-conductive, flexible, water vapor-permeable, electrically-insulating top layer in contact with the current dispersing element. The conductive adhesive material is conductive in a direction substantially orthogonal to a plane of the electrode and semi-conductive in a direction substantially lateral to the plane of the electrode. The water vapor permeability of the electrode can be greater than 100 gm/m2/24 hours.

In one example, an electrode for use with a therapeutic current delivery system can comprise a non-conductive, flexible, water vapor-permeable, electrically-insulating top layer; and a flexible, water vapor-permeable, conductive adhesive material disposed on one side of the electrically-insulating top layer. The conductive adhesive material can be configured to provide conductive paths in both lateral and orthogonal directions to a plane of the electrode. The top layer can be in contact with the conductive adhesive material.

In one example, the electrode can be configured to deliver a defibrillation pulse. The defibrillation pulse can comprise a therapeutic pulse having an energy of at least 200 joules. In another example, the electrode can be configured to deliver at least one pacing pulse. The pacing pulse can comprise a current pulse having a duration in a range of 10-40 ms and an amplitude of at least 50 mAmps.

In an example, the conductive adhesive material can comprise conductive particles distributed in a polymer material to provide the conductive paths. The conductive adhesive material can be configured to substantially distribute a therapeutic current over the plane of the electrode prior to delivery to a subject. In one example, the electrode can further comprise a current dispersing element in contact with the conductive adhesive material. The current dispersing element can be configured to be conductive at least laterally along the plane of the electrode. The water vapor permeability of the electrode can be greater than 100 gm/m²/24 hours.

BRIEF DESCRIPTION OF THE DRAWINGS

These and other features and characteristics of the present disclosure, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limit of the invention.

DESCRIPTION OF THE DISCLOSURE

Figure 1:
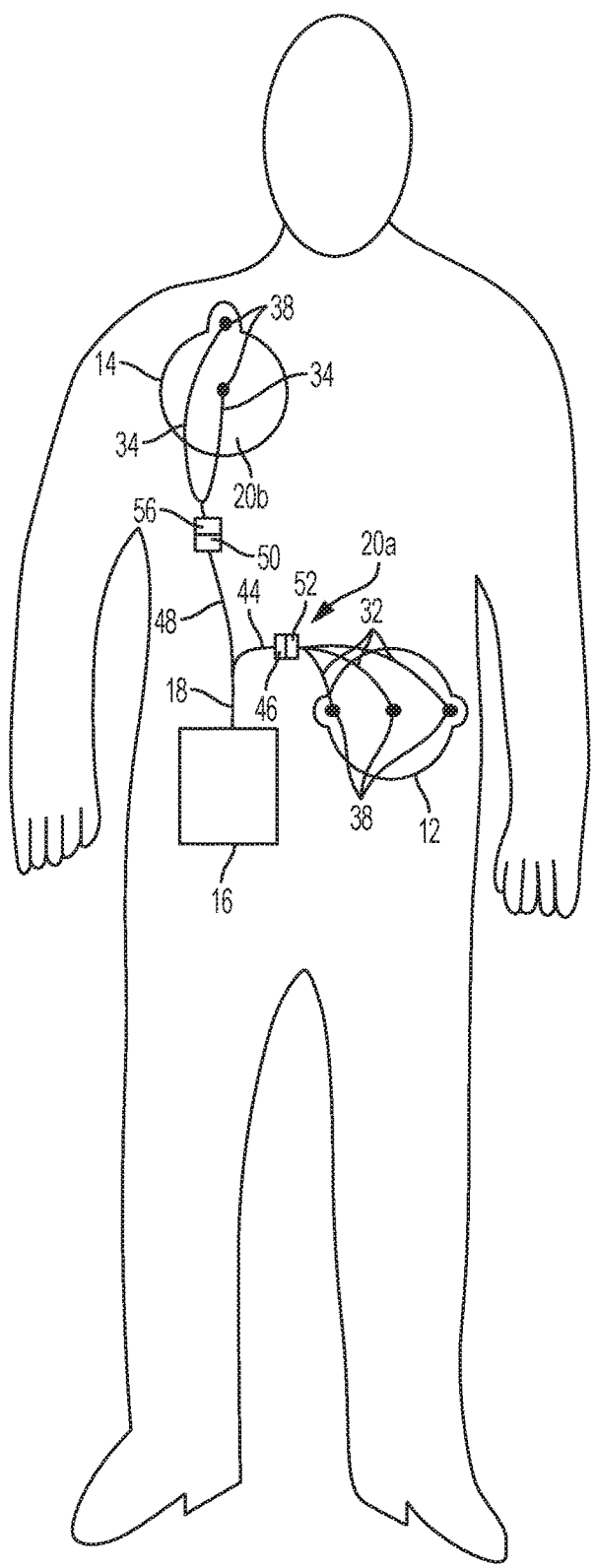
FIG. 1 is a front elevational view of a defibrillation system according to the present disclosure attached to a patient.
Figure 2:
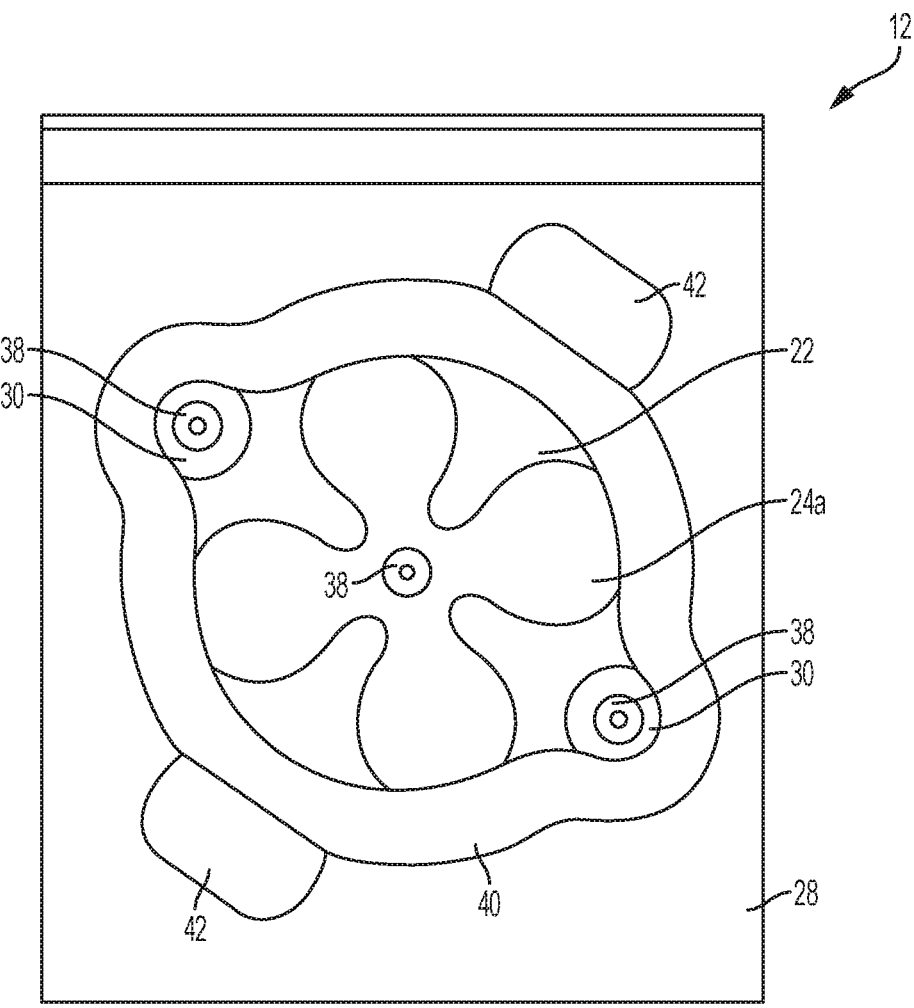
FIG. 2 is a top elevational view of one example of an apex electrode according to the present disclosure having a segmented current dispersing element.
Figure 3:
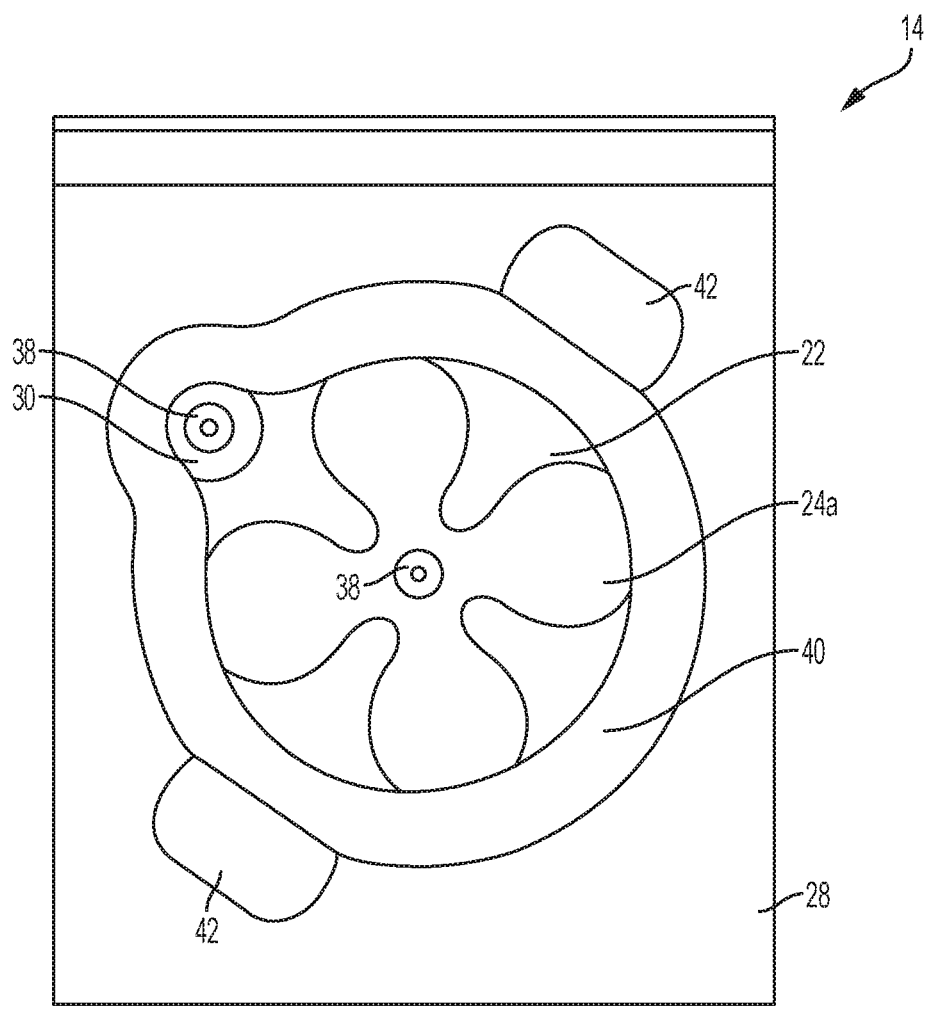
FIG. 3 is a top elevational view of one example of an anterior electrode according to the present disclosure having a segmented current dispersing element.
Figure 4:
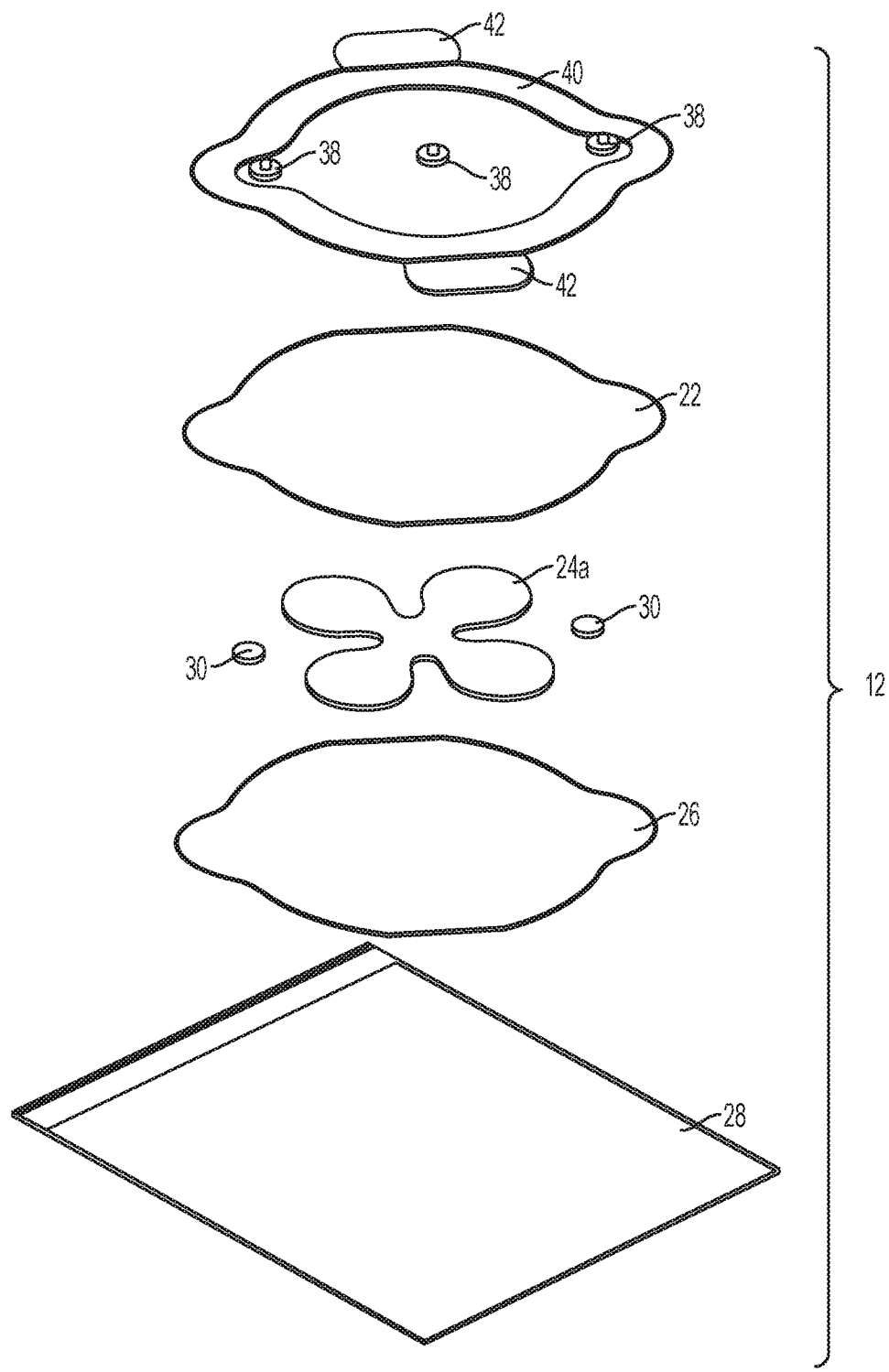
FIG. 4 is an expanded view of the electrode of FIG. 2.
Figure 5:
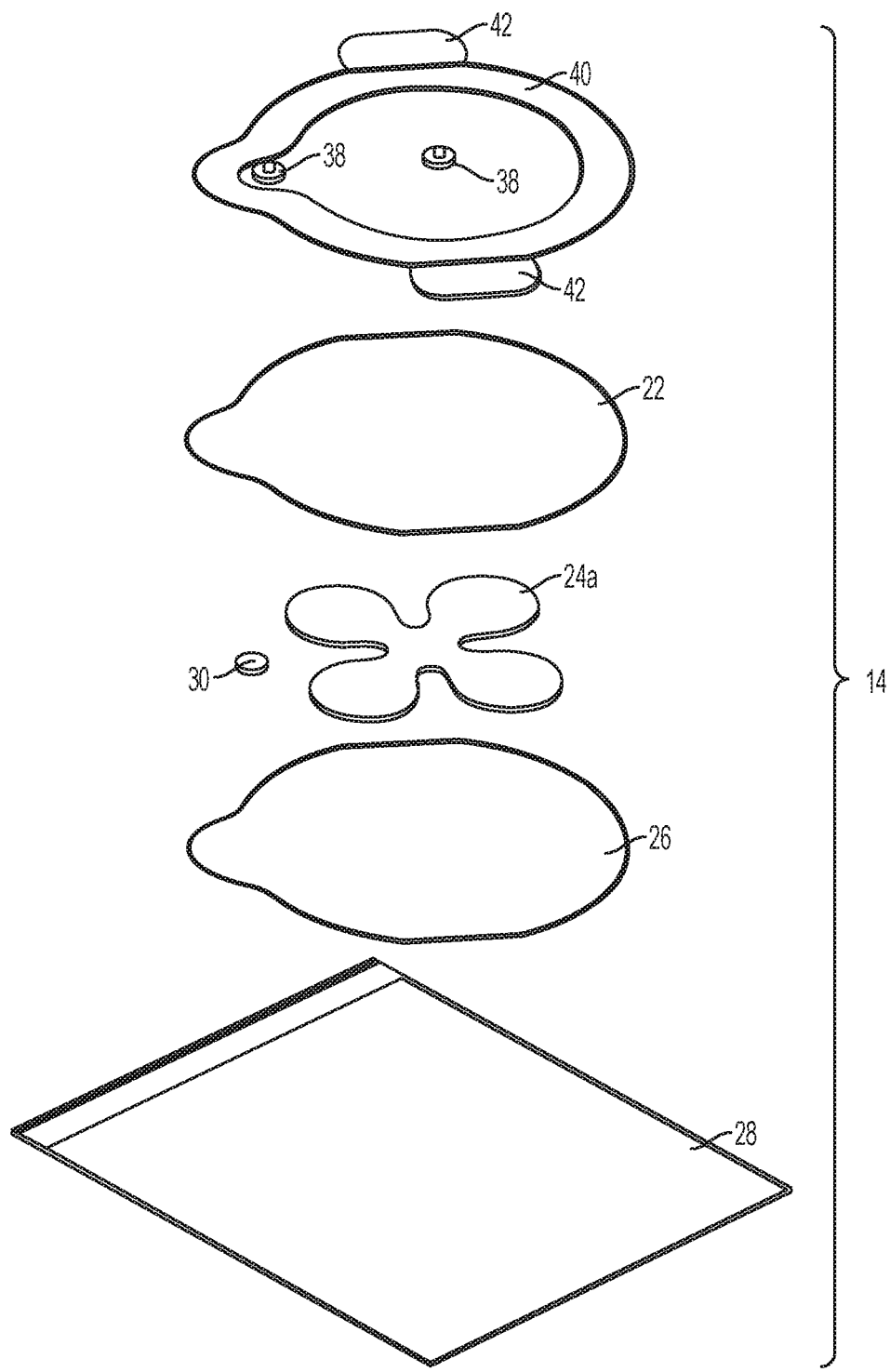
FIG. 5 is an expanded view of the electrode of FIG. 3.

As used herein, spatial or directional terms, such as "inner", "left", "right", "up", "down", "horizontal", "vertical" and the like, relate to the invention as it is described herein. However, it is to be understood that the invention can assume various alternative orientations and, accordingly, such terms are not to be considered as limiting. For the purposes of this specification, unless otherwise indicated, all numbers expressing quantities of ingredients, reaction conditions, dimensions, physical characteristics, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements.

Also, it should be understood that any numerical range recited herein is intended to include all sub-ranges subsumed therein. For example, a range of "1 to 10" is intended to include any and all sub-ranges between and including the recited minimum value of 1 and the recited maximum value of 10, that is, all subranges beginning with a minimum value equal to or greater than 1 and ending with a maximum value equal to or less than 10, and all subranges in between, e.g., 1 to 6.3, or 5.5 to 10, or 2.7 to 6.1.

Biomedical electrodes (referred to herein as simply "electrodes") may be used for defibrillating, pacing, cardioversion, and/or monitoring the activity of a subject's heart. The electrodes disclosed herein are suitable for use on human subjects or patients, although use on non-human subjects is also contemplated. Examples of electrodes as disclosed herein can be coupled with power sources and control logic to deliver electrical energy to a subject, to determine the timing, levels, and history of applied energy, and to process monitored or detected data for analysis by, for example, a health care provider. Examples of electrodes as disclosed herein may be located proximate to the subject, for example, attached, connected, or coupled to the subject, at an anterior, posterior, lateral, or other location on the subject. For example, examples of electrodes as disclosed herein can be attached to the subject's chest, back, side, head, abdomen, torso, thorax, or legs. In some examples, the electrodes disclosed are configured to be attached to the subject proximate to the subject's heart.

In various instances, it may be desirable to provide non-invasive externally placed electrodes for an extended period of time to allow for defibrillation, to pace the heart, and/or to monitor the heart of a subject, for example, while the subject is recovering from a heart attack, surgery, or other injury to the heart, while awaiting a heart transplant, or to monitor and/or protect a subject at risk of syncope. In some prior art externally-attached biomedical electrodes, attachment of the electrodes to the skin of a subject may result in skin irritation at the point of attachment within a relatively short period of time ranging, for example, from about a few hours to about a few days. Extended-wear electrodes in accordance with examples of the present disclosure are constructed of materials, for example, adhesive films and electrically conducting materials, which can reduce the occurrence of skin irritation and/or extend the time for which the electrode may be comfortably attached to the skin of a subject.

In some examples, extended-wear electrodes in accordance with the present disclosure may be worn continuously by a subject for a time period in excess of, for example, three days, for a week or more, or for up to about two weeks or more without the subject experiencing significant skin irritation due to the attachment of the electrode to the skin of the subject. As used herein "significant skin irritation" is defined as corresponding to a skin irritation grading of one (a weakly positive reaction usually characterized by mild erythema and/or dryness across most of the treatment site) or more as set forth in Table C.1 of Annex C of AANI/AAMI/ISO standard 210993-10:2010 when electrodes are tested on human subjects in accordance with the method set forth in this standard. As used herein, the terms "long-term wear" or "extended-wear" refer to continuous or substantially continuous contact of an electrode with the skin of a subject for a time period in excess of, for example, three days, for a week or more, or for up to about two weeks or more. The extended-wear electrodes disclosed herein can have the ability to apply a defibrillation charge to, or perform cardioversion on, a subject wearing the electrodes and may, in addition, monitor and/or pace the heart of a subject. Examples of the electrodes disclosed herein may be compliant with the ANSI/AAMI DF80:2003 medical electrical equipment standard for the safety of cardiac defibrillators.

As discussed above, conventional electrodes using vapor impermeable materials may trap vapor emanating from the surface of a patient's skin. The water vapor emanating from intact skin can be significant, on the order of 240-1,920 $g/m^2$ per 24 hours [Thomas S. *Handbook of Wound Dressings*. Macmillan: London, 1994]. In contrast, in some examples, the extended-wear electrodes in accordance with the present disclosure may provide for the passage of water vapor, for example, a patient's sweat, through the electrode to facilitate reduction in skin irritation, for example when the electrode is used for "long-term wear" or "extended-wear" regimens. Extended-wear electrodes in accordance with the present disclosure may exhibit a moisture vapor transmission rate (MVTR) of, for example, between about 600 $g/m^2$/day and about 1,400 $g/m^2$/day when worn by a subject in an environment at room temperature (e.g., about 25° C.) and at a relative humidity of, for example, about 70%.

In some systems, the defibrillator, TCP, or other device capable of delivering therapeutic electrical current may be incorporated into a wearable device in which case such a device can continuously monitor the physiologic status of the patient over an extended period of time of hours, days, and even months. In such cases, the wearable therapeutic system can be configured to be light and comfortable enough for a patient to be able to sleep, walk, and engage in all the normal daily activities. In particular, the current-carrying electrodes for delivery of the therapeutic electrical current may be configured such that electrical contact be made between the conductive element of the electrode and the patient's skin at the time of delivery of the therapeutic current, while at the same time be wearable for extended periods without damage to the patient's skin.

Extended-wear electrodes in accordance with examples of the present disclosure may provide one or more advantages over prior art electrodes, for example the ability to wear the electrodes for an extended period of time may reduce the number of electrodes consumed over a given period of time, reducing the cost associated with replacing electrodes which are not suitable for use in extended-wear scenarios, for example, for time periods greater than about a week.

Discomfort of a subject associated with wearing the electrodes may be decreased due to a reduction in skin irritation caused by the extended-wear electrodes as compared to conventional electrodes. Discomfort of a subject associated with wearing the electrodes may also be decreased due to a reduction in the number of times which an extended-wear electrode may need to be removed from the skin of the subject or repositioned, resulting in possible damage to the underlying skin, as compared to conventional electrodes. Further, accuracy of monitoring of the heart of a subject may be facilitated by the use of extended-wear electrodes by keeping the monitoring electrodes in the same position rather than replacing them and mounting them in potentially different positions as may occur with electrodes which should be replaced frequently or repositioned due to the occurrence of skin irritation.

Electrodes in accordance with some examples of the present disclosure may be combined as part of a long-term wear device, for example, as part of known non-invasive bodily-attached ambulatory medical monitoring and treatment devices, such as the Life Vest® Wearable Cardioverter Defibrillator available from ZOLL Medical Corporation. Electrodes in accordance with some examples of the present disclosure may be used in syncope monitoring and/or treatment devices such as described in U.S. patent application Ser. No. 13/907,406, titled SYSTEMS AND METHODS FOR DETECTING HEALTH DISORDERS, the disclosure of which is incorporated by reference herein in its entirety.

As shown in FIG. 1, two electrodes 12, 14 may be connected to a wearable defibrillator/monitor 16 via a cable harness 18 and cable connectors 20a, 20b. The defibrillator/monitor 16 may communicate with the electrodes 12, 14 to monitor the patient, provide pacing impulses to the patient, and to transmit defibrillation energy to the patient. While a wearable defibrillator/monitor 16 is described with reference to FIG. 1, this is not to be construed as limiting the present disclosure, as any suitable therapeutic current delivery system may be utilized with the electrodes 12, 14 disclosed herein, such as a pacing device or a transcutaneous electrical nerve stimulation device. If a defibrillation system is used, an energy setting can be in a range of 150-360 Joules. For example, the energy setting can be about 200 Joules. In some examples, if a pacing device is used, an initial energy setting may be configured to have the device deliver through an electrode a 10-40 ms current pulse of energy at a current of at least 50 mAmps.

In one example, two electrodes 12, 14 may be used. An apex electrode 12 is placed on the patient's left abdomen and back and an anterior electrode 14 is placed on the patient's upper right chest as shown in FIG. 1. The electrodes 12, 14 may be provided, for example, to apply electrical treatment or shock, or may further comprise at least one sensing element 30 as shown in FIGS. 2-7. For example, the apex electrode 12, shown in FIGS. 2, 4, and 6, can include, e.g., two sensing elements 30, and the anterior electrode 14, shown in FIGS. 3, 5, and 7, can include, e.g., one sensing element 30.

In one example, the electrodes 12, 14 can comprise a conductive, water vapor-permeable adhesive material that is configured to be positioned against the skin of a patient. The conductive adhesive material provides the function of adhesion and conduction of current primarily in the Z-axis direction (orthogonal to the plane of the electrode). The electrodes 12, 14 can also comprise a current dispersing element such as, but not limited to, a conductive mesh. The current dispersing element provides the function of current dispersal in the X-Y directions (laterally, along the plane of the electrode) to ensure the current distribution is more uniform, thus preventing burning of the patient's skin as a result of therapeutic current delivery that is uneven across the face of the electrode and causing electrical current burns on the patient. The electrodes 12, 14 can also comprise an outermost layer away from the patient's skin. This layer provides the functions of electrical insulation, preventing shocks to bystanders, and functions as a water-resistant or waterproofing layer so that the electrodes 12, 14 may be worn in the shower or while bathing.

Referring to FIGS. 2-7, prior to application to the skin of the patient, each electrode 12, 14 comprises: at least one non-conductive, flexible, water vapor-permeable, electrically insulating top layer 22 that provides, e.g., protection from short circuiting of the electrode against adjacent conductive objects in the vicinity of the patient during a defibrillation shock; a current dispersing element 24a, 24b, e.g., comprising or made from a flexible, conductive, water vapor-permeable mesh providing enhanced conductivity and mechanical support; a flexible, water vapor-permeable, conductive adhesive material 26 for contact with the patient's skin; and optionally a removable backing 28.

Figure 8:
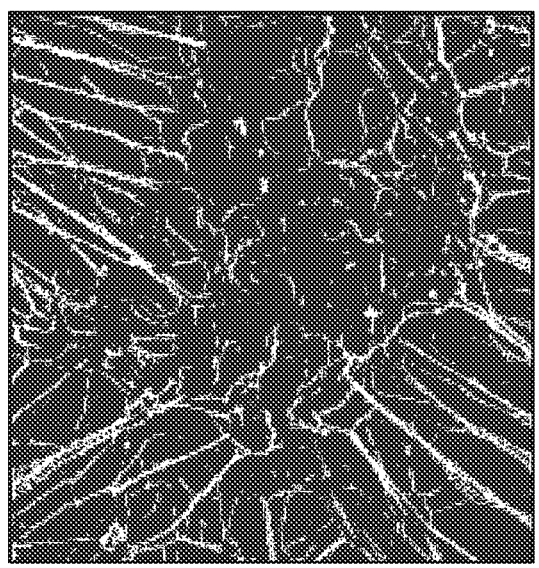
FIG. 8 is a photograph of an electro-spun polyurethane adhesive as used for the flexible, water vapor-permeable, conductive adhesive layer of the present disclosure.

The flexible, water vapor-permeable, conductive adhesive material 26 for contact with the patient's skin may comprise or be made from materials including, but not limited to, a spun adhesive polymer such as an electro-spun polyurethane adhesive, for example, as described in Khil et al., "Electrospun Nanofibrous Polyurethane Membrane as Wound Dressing", Journal of Biomedical Materials Research Part B: Applied Biomaterials, 67(2), pp. 675-679, 2003, the disclosure of which is incorporated by reference herein in its entirety, and as shown in FIG. 8.

Figure 9:
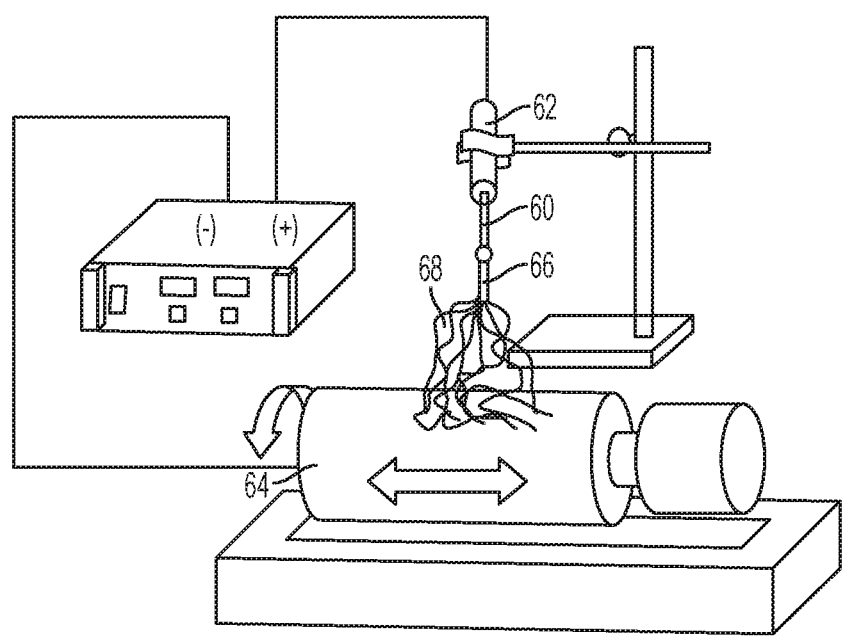
FIG. 9 is a schematic of the apparatus used to make the electro-spun polyurethane adhesive of FIG. 8.

In one example, such electrospun polyurethane adhesive can be produced using an electrospinning setup shown in FIG. 9. Polymer solutions are injected through a syringe 60. A positive electrode 62 is inserted into the solution and a rotational collector 64 is placed at an appropriate distance from the tip of the syringe 60 to act as a grounded counter electrode. As an electrical potential is applied, a polymer stream 66 is created. The polymer stream 66, formed by electrical forces, follows a complicated stretching and looping pattern as it solidifies. The resulting fibers 68 are collected on the rotational collector 64 to produce a sheet of membrane.

In order to achieve conductive qualities in the flexible, water vapor-permeable, conductive adhesive material 26, conductive particles may be injected into the housing containing the apparatus of FIG. 9. The conductive particles may be microscopic or nano-scale particles or fibers of materials, including but not limited to, one or more of carbon black, silver, nickel, graphene, graphite, carbon nanotubes, and/or other conductive biocompatible metals such as aluminum, copper, gold, and/or platinum. The conductive particles may be sprayed into the housing where the electrospinning is occurring and are charged with the opposite polarity as the polymer stream 66. The conductive particles are attracted to and bonded to the polymer stream 66 resulting in a conductive adhesive sheet.

Alternatively, the flexible, water vapor-permeable, conductive adhesive material 26 may be fabricated via such known means for creating polymerized microemulsion pressure sensitive adhesives as described in U.S. Pat. No. 5,670,557, the disclosure of which is incorporated by reference herein in its entirety. During the mixing process of the microemulsion, the previously described conductive particles are added and dispersed into the microemulsion. The conductive particles may further be treated to preferentially attract to one or the other of the two domains of the microemulsion. Thus, if one domain is designed to evaporate, leaving a microporous structure, the conductive particles will reside in the evaporating layer, and then eventually coat the inside walls of the porosities in the final film. Alternatively, an electroplating process can be used to plate copper, silver chloride, or other metal onto the inner walls of the microporous structure.

Alternatively, an appropriate organic conductive or semi-conductive polymer or other compound, such as poly(3,4-ethylene dioxitiophene), doped with poly(styrene sulfonate), (PEDOT:PSS) poly(aniline) (PANI), poly(thiopene)s like poly(3-hexylthiophene) (P3HT) and poly(9,9-dioctylfluorene co-bithiophen) (F8T2) can be used to prepare the conductive adhesive. Such polymers can be printed as a flexible, water vapor-permeable, conductive adhesive layer using such methods as inkjet printing, screen printing, offset printing, flexo printing, and gravure printing.

The flexible, water vapor-permeable, conductive adhesive material 26 is designed to be sufficiently conductive in a direction substantially orthogonal to a plane of the electrode (i.e., in the Z-axis) by, e.g., controlling both its thickness and a density and shape of the conductive particles that are dispersed in the adhesive polymer matrix. Composite material properties, which result when conductive particles are dispersed into a polymer matrix, may be influenced by the particle volume fraction. The conductive paths are formed by metal particles. At critical concentration, a connected chain network of particles first appears in the system. As the particle concentration is increased, the fraction of particles in this network increases. Such a network can contribute to the major conduction process. This is known as Percolation Theory of conductive adhesives. Several factors are known to affect the magnitude of the threshold volume fraction, such as particle size distribution, particle shape, and pretreatment of the particle. For an adhesive that is preferentially conductive in the Z-direction, the volume loading of conductive particles can be on the order of 5-25% by volume. The geometry of the conductive particles themselves may be approximately spheroidal, flake, or needle-like. The size of the conductive particles may be in the range of, though not limited to, about 1 to about 100 μm. While the conductive adhesive layer 26 may range in thickness from 0.25 to 50 thousandths of an inch or more, in some implementations the thickness is about 1 to 10 mils. The conductive particles may also be nano-sized particles. The conductive particles may be pre-treated with an etchant such as phosphoric acid, and/or coated with an interfacial coupling agent such as a silane. The silane may be designed to provide some level of semi-conductivity or conductivity. Alternative coupling agents such as thiols, carboxylate, or others may also be used. Such adhesives are discussed in detail in Sancaktar, E. et al., "Electrically Conductive Epoxy Adhesives", *Polymers*, vol. 3, pp. 427-466, 2011, the disclosure of which is incorporated by reference herein in its entirety.

The current dispersing elements 24a, 24b may comprise a flexible, conductive mesh that can provide enhanced conductivity and mechanical support for the structure or any other suitable flexible, conductive material. Without it, the flexible, water vapor-permeable, conductive adhesive material 26 can be insufficiently conductive in the lateral (X-Y) direction to carry defibrillation current through the cable connectors 20a, 20b to the patient without substantial current or voltage degradation. The mesh may be a simple metallic mesh composed, for example, of copper, tin, nickel, silver, gold, and/or other conductive, biocompatible material as discussed in detail above. The gauge and weave of the mesh are designed to be conformable to the body. Generally, the gauge of the wire is higher than 22 AWG (smaller diameter, less than 0.0253 inches). In some examples, the gauge is around 60 AWG, with the mesh opening spaces making up at least 30% of the mesh surface area. In some examples, the mesh occupies less than 15% of the surface area of a plane defined by the mesh. In other examples, the mesh may comprise nickel-plated carbon-filled fibers. The current dispersing elements 24a, 24b may be formed into the conductive adhesive material 26, during the polymerization of the conductive pre-polymer solution, thereby creating a single structure that incorporates the functionality of both the current dispersal element 24a, 24b and the adhesive 26. In addition, the conductive adhesive material 26 is not required to be a sheet or continuous film interposed between the current dispersing elements 24a, 24b and the patient's skin. In one example, the conductive adhesive material 26 can be sprayed or applied as a coating onto the current dispersing elements 24a, 24b.

In one example, the current dispersing elements 24a, 24b can be positioned between the flexible, water vapor-permeable, conductive adhesive layer 26 and a non-conductive, flexible, water vapor-permeable, electrically-insulating top layer 22 as discussed in greater detail hereinafter.

In some examples, the current dispersing elements 24a, 24b is adhered to the conductive adhesive layer 26 by positioning the current dispersing elements 24a, 24b in contact with or facing engagement with at least a portion of the adhesive portion, such that at least the contacting portion of the current dispersing elements 24a, 24b is adhered to the adhesive material 26. In some examples, the optional removable backing 28 can be adjacent to the adhesive material 26 prior to contact with the current dispersing elements 24a, 24b, and heat and/or pressure can be applied to form an adhesive bond between the current dispersing elements 24a, 24b and the adhesive material 26. The adhesive material itself may be designed to bond self-adhesively to the other layers in contact with it. Additional current dispersing materials may be interposed between the current dispersing elements 24a, 24b and the conductive adhesive material 26. The additional current dispersing material may take the form of sprayed conductive nano- or micro-particles such as carbon black or nickel flake. For example, this can improve current uniformity in the case when the current dispersing element is made of a metallic wire mesh.

The top layer 22 is generally non-conductive, flexible, water vapor-permeable, electrically-insulating, and optionally at least substantially liquid-impermeable or waterproof. The non-conductive flexible, water-vapor permeable, electrically-insulating top layer 22 may comprise or consist of polyurethane, such as Tegaderm™ polyurethane film (available from 3M), Opsite™ polyurethane film (available from Smith & Nephew), or Hydrofilm™ polyurethane film (available from Hartman USA). The top layer 22 can provide some protection from defibrillation current inadvertently shocking someone close to the patient. In addition, where the top layer 22 is waterproof, the extended-wear electrodes disclosed herein may be worn when the user is showering.

With respect to the top layer 22, as used herein, the term "non-conductive" means impedance in excess of 1000 ohms by the Z-axis Impedance Measurement Method 1 discussed hereinafter. With respect to the top layer 22, as used herein, the term "electrically-insulating" means using the test set-up of Z-axis Impedance Measurement Method 1 discussed hereinafter, then applying 120+/−10 VDC, 15 second duration, with leakage current not to exceed 100 microamps. With respect to the top layer 22, as used herein, the term "liquid-impermeable" means waterproof per AATCC 127-2014. In some embodiments, the top layer 22 may be composed of Tegaderm, and the top layer 22 contains its own adhesive with which the Tegaderm is affixed to the underlayers of the current dispersing elements 24a, 24b, or alternatively may be a GORE-TEX® PTFE film that is adhesively affixed to the underlayers. The top layer 22 in some implementations has a larger diameter than the other sublayers, thus providing an adhesively-sealed perimeter that provides both waterproofing as well as enhanced electrical insulation.

In an example, the electrodes 12, 14 are a laminate structure with the adhesive material 26, the current dispersing elements 24a, 24b, and the top layer 22 being aminated together. In such an example, the flexural rigidity of the electrodes 12, 14 is, by necessity, is equal to or greater than the flexural rigidity of each individual components. The overall flexural rigidity of the electrodes 12, 14 can be less than 40 grams/cm², as measured using the ASTM D1388-14, "Standard Test Method for Stiffness of Fabrics". This standard requires the electrode 12, 14 to be slid at a specified rate in a direction parallel to its long dimension until its leading edge projects from the edge of a horizontal surface. The length of the overhang is measured when the tip of the specimen is depressed under its own mass to a point where the line joining the top to the edge of the platform makes a 41.5° angle with the horizontal. From this measured length, the bending length and flexural rigidity are calculated using the following equations.

$$c = O/2$$

where:
 $c$=bending length, mm; and
 $O$=length of overhang.

$$G = 1.421 \times 10^{-5} \times W \times c^3$$

where:
 $G$=flexural rigidity;
 $W$=fabric mass per unit area; and
 $c$=bending length.

In addition, in one example, the vapor permeability of the electrodes 12, 14 is greater than 100 gram/meter²/24 hours, as measured by such vapor transmission standards of ASTM E-96-80 (Version E96/E96M-13), using either the "in contact with water vapor" ("dry") or "in contact with liquid" ("wet") methods discussed in greater detail hereinafter.

The electrodes 12, 14 may be used to deliver other forms of high-power therapeutic electrical current to the patient other than defibrillation, for instance external TCP used to keep a bradycardic heart beating at a normal rate or other cardiac conditions. "High power" is here considered an electrical pulse in excess of 1 Joule or 20 milliamps.

The present disclosure is not limited to any particular shape for the electrode, or of the components thereof, and any one or more components of an electrode in accordance with the present disclosure may have different shapes than those illustrated. For example, the current dispensing element 24a can be segmented with a low surface area and high perimeter as compared to a circular or square electrode and as shown in FIGS. 2-5 where the current dispersing element 24a takes a clover shape having four circular segments. The overall size and shape of the current dispersing element 24a may differ from that of the adhesive material 26 and/or the top layer 22. Overall area for the electrode when used in pacing or defibrillation can be about 25-200 inches².

Figure 6:
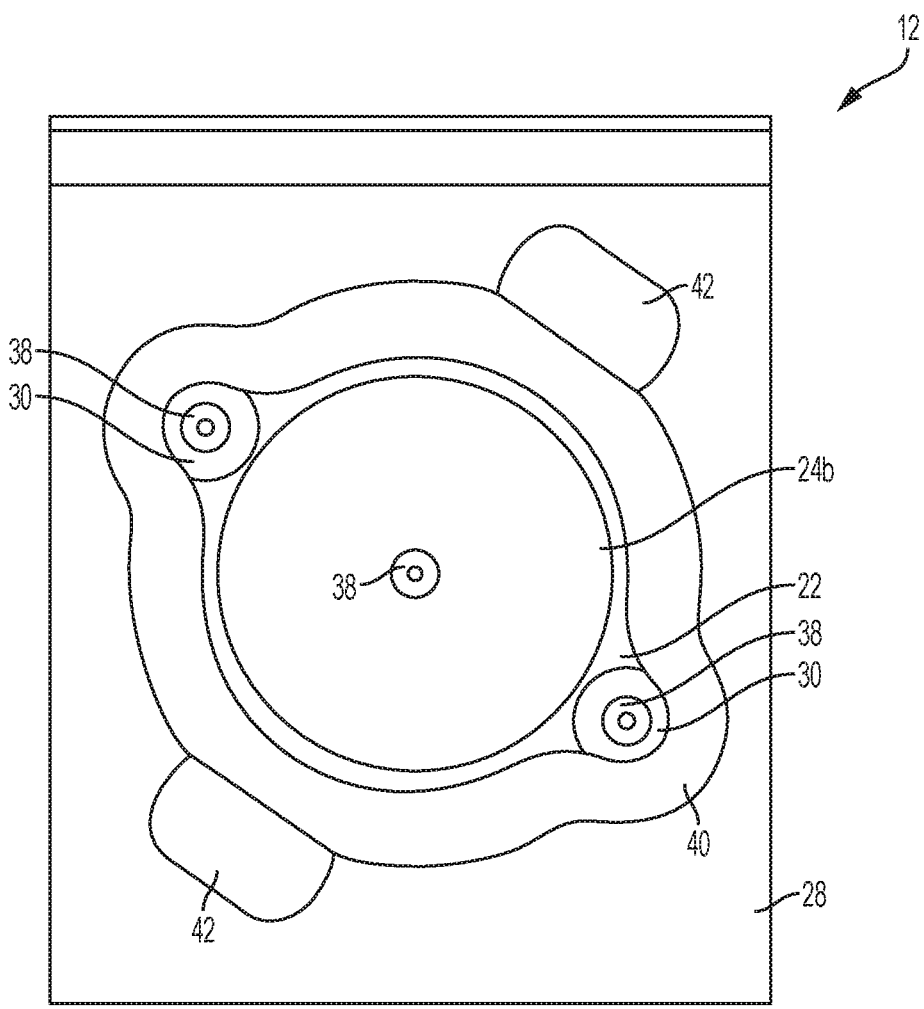
FIG. 6 is a top elevational view of one example of an apex electrode according to the present disclosure having a non-segmented current dispersing element.
Figure 7:
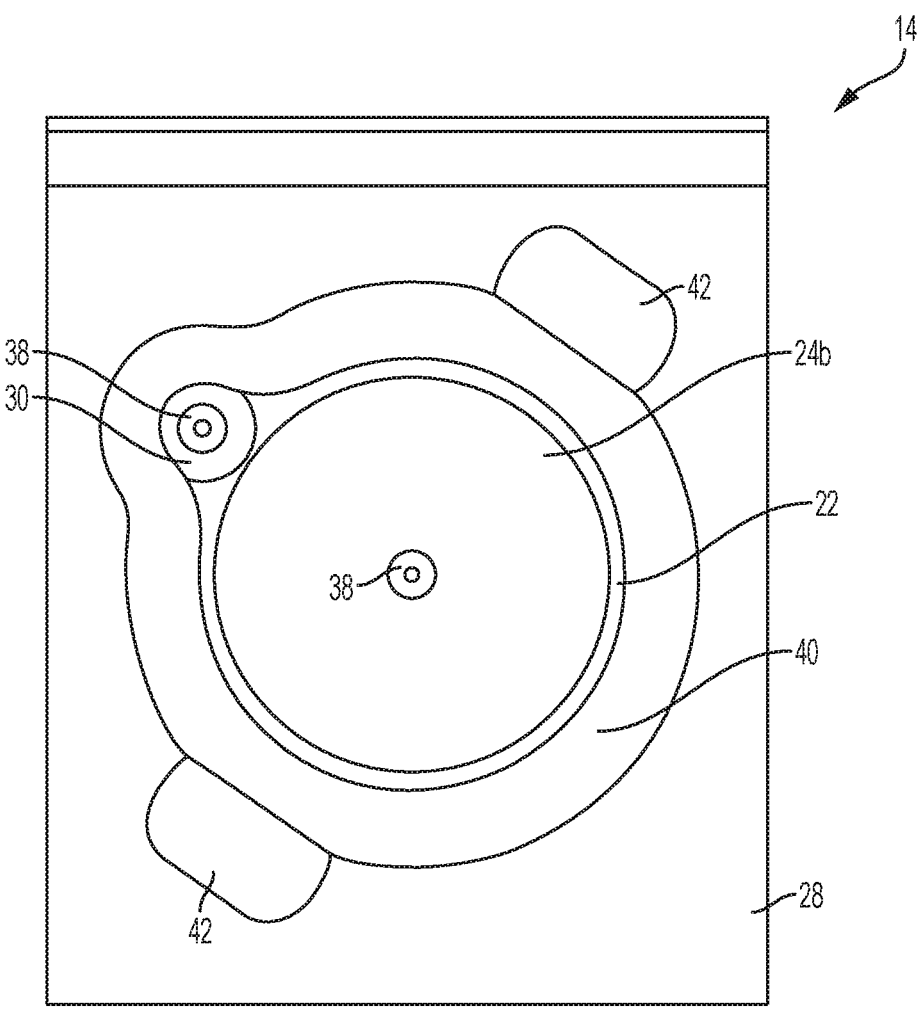
FIG. 7 is a top elevational view of one example of an anterior electrode according to the present disclosure having a non-segmented current dispersing element.

Alternatively, the current dispersing element 24b may be non-segmented and may be oval, triangular, square, pentagonal, or any other shape desired. As shown in FIGS. 6 and 7 for example, the current dispersing element 24b is a single, large circle.

A small area of the non-conductive, flexible, water vapor-permeable, electrically-insulating top layer 22 is relieved to expose a small area, of approximately 0.25 square inches±90%, of the current dispersing elements 24a, 24b. Wires 32, 34 (shown in FIG. 1) of the cable connectors 20a, 20b are attached to the electrodes 12, 14 by a connector, such as a rivet or clamp mechanism directly to the current dispersing elements 24a, 24b, and an additional small piece(s) of adhesive material 26 may be used to cover any small regions of exposed conductive surfaces in the area of the attachment.

In some examples, backing 28 can be attached to the adhesive material 26. The backing 28 extends beyond the outer surfaces of the electrodes 12, 14 in order to provide an area for the user to grasp the backing 28 when removing it from the electrodes 12, 14 for placement on the patient. The backing 28 may be made from liners made of or coated with polyethylene, polypropylene, and fluorocarbons and silicone coated release papers or polyester films, for example.

If present, the sensing elements 30 can be positioned between the flexible, water vapor-permeable, conductive adhesive material 26 and the non-conductive, flexible, water vapor-permeable, electrically-insulating top layer 22. The sensing elements 30 may be made of a core plastic or metal substrate element that is coated with a thick-film polymeric compound filled with a conductive Ag/Ag/Cl metallic filler, as is currently used by most ECG electrode manufacturers such as Biodetek (Pawtucket, R.I.). Alternatively, the sensing function may be provided by the electrodes 12, 14 themselves, and the separate sensing element is eliminated.

Both the current dispersing elements 24a, 24b and the sensing element 30 may include a portion which extends through the top layer 22 to contact an electrical connector 38 (shown in FIG. 1). The electrical connector 38 may include a protrusion that acts as a snap for connection of the wires 32, 34 of the cable connectors 20a, 20b or may take any other suitable form including, but not limited to a structure suitable for attaching an alligator clip. Alternatively, the wires 32, 34 of the cable connectors 20a, 20b may be directly hard wired to the current dispersing elements 24a, 24h and/or the sensing element 30 as described above.

Alternatively, the current dispersing elements 24a, 24b could be used both for defibrillation and sensing and the sensing elements 30 could be eliminated.

As can be seen in FIGS. 2-7, the top layer 22 can be configured to completely cover the current dispersing elements 24a, 24b and the sensing element 30. However, the surface area of the top layer 22 is minimized as much as possible so that the amount of the patient's skin that is subjected to possible irritation is minimized. Along these lines, it can be seen when comparing FIGS. 2, 4, and 6 to FIGS. 3, 5, and 7, that when using the segmented current dispersing element 24a, the sensing elements 30 can be moved closer to the center of the electrodes 12, 14 than when using the non-segmented current dispersing element 24b, thus reducing the overall area of the electrodes 12, 14.

A frame 40 may be provided on the outer surface of the top layer 22 to give some structural stability to the electrodes 12, 14 after being removed from the backing 28 and before being placed on the patient's skin. The frame 40 may cover the entire surface of the top layer or, as shown in FIGS. 2-7, may be disposed only around the perimeter of the electrodes 12, 14 extending a short distance toward the center of the electrodes 12, 14. The frame 40 may include any number or shape of extensions or tabs 42 that extend beyond the perimeter of the electrodes 12, 14 to assist in removal of the electrodes 12, 14 from the backing 28 for placement on the patient's skin, and the frame 40 from the electrodes 12, 14 after the electrodes 12, 14 have been placed on the patient's skin. The frame 40 may also include one or more perforations or score lines to assist in its removal.

In use, the backing 28 is peeled from the electrodes 12, 14. The electrodes 12, 14 are placed on the patient's skin and pressed into place. The frame 40 is then removed from the electrodes 12, 14.

The electrodes 12, 14 can be capable of undergoing, without failure, at least one current pulse delivered by a current generating device, such as a defibrillator or pacemaker, the pulse being of at least 1 millisecond in duration and 200 volts peak and at least 1 Ampere peak.

Vapor Permeability

As mentioned hereinabove, the electrodes 12, 14 are vapor permeable to allow the electrodes 12, 14 to be worn continuously by the patient for more than 24 hours. Vapor permeability of the complete electrode assembly is greater than 100 gram/m$^2$/24 hours, as measured by such vapor transmission standards of ASTM E-96-80 (Version E96/E96M-13), using either the "in contact with water vapor" ("dry") or "in contact with liquid" ("wet") methods. Such test methods are described in U.S. Pat. No. 6,548,727, the disclosure of which is incorporated by reference herein in its entirety. These test methods are discussed in additional detail below.

Moisture Vapor Transmission Rate (Standard "Dry" Method)

A sample (3.5-cm diameter) is placed between adhesive-containing surfaces of two foil adhesive rings, each having a 2.54-cm diameter hole. The holes of each ring are carefully aligned. Finger pressure is used to form a foil/sample assembly that is flat, wrinkle-free, and has no void areas in the exposed sample.

A 120-mid glass jar is filled to the halfway level with deionized water. The jar is fitted with a screw-on cap having a 3.8-cm diameter hole in the center and a 4.45-cm diameter rubber washer having a 2.84-cm diameter hole in its center. The rubber washer is placed on the lip of the jar and the foil/sample assembly is placed on the rubber washer. The lid is then screwed loosely on the jar.

The assembly is placed in a chamber at 38° C. and 20% relative humidity for four hours. At the end of four hours, the cap is tightened inside the chamber so that the sample is level with the cap (no bulging) and the rubber washer is in the proper seating position.

The foil/sample assembly is then removed from the chamber and weighed immediately to the nearest 0.01 gram (initial weight W1). The assembly is then returned to the chamber for at least 18 hours, after which it is removed and weighed immediately to the nearest 0.01 gram (final weight W2). The moisture vapor transmission (MVTR) in grams of water vapor transmitted per square meter of sample area in 24 hours is calculated according to the following formula (where "T1" refers to exposure time in hours):

$$\text{"Dry"MVTR} = (W1 - W2)(4.74 \times 104) \div T1$$

Three measurements are taken and averaged, and the "dry" MVTR value is reported as grams/m$^2$/24 hrs.

Moisture Vapor Transmission Rate (Inverted "Wet" Method)

The inverted "Wet" Moisture Vapor Transmission Rate (Standard "Dry" Method) (MVTR) is measured using the following test procedure. After obtaining the final "dry" weight (W2) as described for the "dry" MVTR procedure, the assembly is returned to the chamber (38° C. and 20% relative humidity) for at least 18 additional hours with the sample jars inverted so that the deionized water is in direct contact with the test sample. The sample is then removed from the chamber and weighed to the nearest 0.01 gram (final "Wet" weight, W3). The inverted "Wet" MVTR in grams of water vapor transmitted per square meter of sample area in 24 hours is calculated according to the following formula (where "T2" refers to exposure time in hours):

$$\text{Inverted"Wet"MVTR} = (W2 - W3)(4.74 \times 104) \div T2$$

Three measurements are taken and averaged, and the "wet" MVTR value is reported as g/m$^2$/24 hrs.

Peel Adhesion

The electrode 12, 14 also meets the peel adhesion test established by the Pressure Sensitive Adhesive Tape Council of Chicago, Ill. ("PSTC"): namely, PSTC-1 (11/75) entitled "Peel Adhesion for Single Coated Tapes 180° Angle", ("PSTC-1 Test"), the disclosure of which is incorporated by reference herein in its entirety. This test is described in U.S. Pat. Nos. 5,670,557, 4,952,650, and 4,833,179, the disclosures of which are incorporated by reference herein in their entireties. The PSTC-1 Test determines peel adhesion as the force required to remove a pressure sensitive adhesive tape from a panel or its own backing at a specified angle and speed. The electrode 12, 14 has a peel adhesion of at least 3 N/100 mm as determined by the PSTC-1 Test. This test method is discussed in additional detail below.

Peel Adhesion Test

Peel adhesion is the force required to remove a coated flexible sheet material from a test panel measured at a specific angle and rate of removal. This force is expressed in Newtons per 100 mm (N/100 mm) width of coated sheet. A 12.5 mm width of the coated sheet is applied to the horizontal surface of a clean glass test plate with at least 12.7 lineal cm in firm contact. A hard rubber roller is used to apply the strip. The free end of the strip is doubled back nearly touching itself, so the angle of removal will be 180°. The free end is attached to the adhesion tester scale. The glass test plate is clamped in the jaws of a tensile testing machine which is capable of moving the plate away from the scale at a constant rate of 2.3 meters per minute. The scale reading in Newtons is recorded as the tape is peeled from the glass surface. The data is recorded as the average value of the range of numbers observed during the test.

Impedance

Impedance of the disclosed electrode may be measured in three different ways as described in "3M™ Electrically Conductive Cushioning Gasket Tape ECG-8035/ECG-8055/ECG-8075", Technical Data, February, 2010, the disclosure of which is incorporated by reference herein in its entirety.

Z-Axis Impedance Measurement Method 1

Figure 10A:
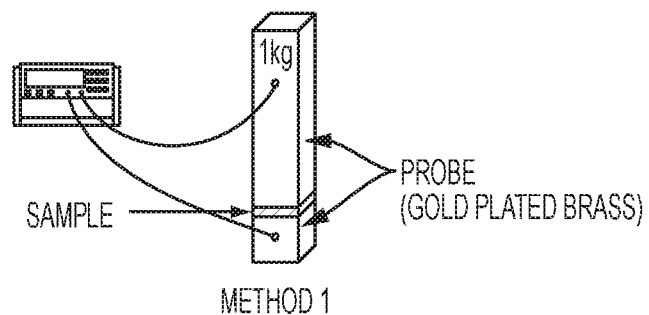
FIGS. 10A and 10B are schematic representations of the equipment and set-up used to perform the two disclosed methods for measuring Z-axis impedance.

As shown in FIG. 10A, a 25.4 mm×25.4 mm sample is placed between two 25.4 mm×25.4 mm gold plated brass probes, and the sample assembly is placed under a 1 kg load. The impedance is measured using a 60 second dwell time and reported in ohms ($\Omega$). Using this method, the Z-axis impedance of the conductive adhesive material 26 is less than 25 ohms.

Z-Axis Impedance Measurement Method 2

Figure 10B:
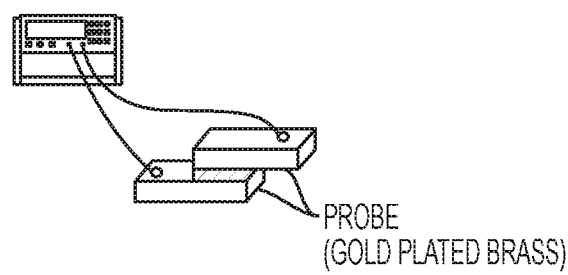

As shown in FIG. 10B, a 10 mm×10 mm sample is placed between two gold plated brass probes. The impedance is measured using a 60 second dwell time without any load and reported in ohms ($\Omega$). Using this method, the Z-axis impedance of the conductive adhesive material 26 is less than 50 ohms. Satisfying these two test methods can constitute "conductive" in the Z-axis direction.

Surface Impedance Measurement

The surface of a sample is contacted by a 25 mm×25 mm Cu plate for 10 seconds and the impedance is measured and reported in ohms sq. ($\Omega$/☐). Using this method, the surface impedance of the conductive adhesive material 26 is less than 100 ohms/sq.

X-Y Axis Impedance Measurement

A 25.4 mm×75 mm wide strip of conductive adhesive material is cut out. 25 mm of the length is adhered to one of the 25.4 mm wide gold plated brass probes of FIG. 10A, and then the upper probe is placed on top as in the figure. At the other end of the strip, a 25 mm is adhered in the same fashion to a second pair of probes. Impedance is then measured along the length of the strip. Using this method, the impedance shall exceed 5 ohms. Satisfying this test condition constitutes "semi-conductive" in the X-Y directions.

The same X-Y axis Impedance Measurement is performed for the current dispersing element. Using this method, the impedance shall be less than 5 ohms. Satisfying this test condition shall constitute "conductive" in the X-Y directions. In some examples, the current dispersing element is also conductive in the Z-direction such that the current dispersed in the X-Y direction is guided to the conductive adhesive 26 and to the patient.

For the case when the electrodes are to be used for defibrillation, the impedance of the electrodes when measured using the AAMI DF-2 large signal impedance test shall not exceed 10 ohms.

Figure 11:
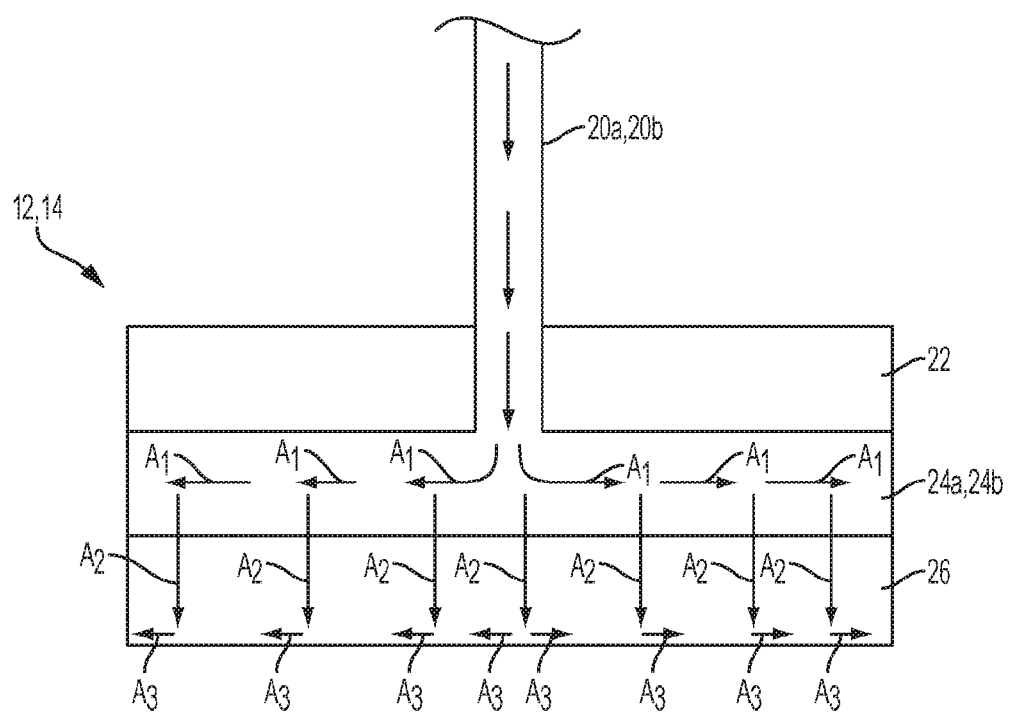
FIG. 11 is a schematic cross-sectional view of an example of an electrode according to the present disclosure.

With reference to FIG. 11, for example, current from the cable connector 20a is provided to the current dispersing elements 24a, 24b, which is conductive at least laterally along the plane of the electrodes 12, 14 as denoted by arrows $A_1$. Accordingly, the current dispersing elements 24a, 24b are conductive at least in the X-Y direction and distribute an electric current over a plane of the electrode. Further, at a plurality of points along the current dispersing elements 24a, 24b, the current can move downward in the Z-axis direction. Accordingly, the current dispersing elements 24a, 24b are conductive in a direction orthogonal to the plane of the electrode or conductive in the Z-axis direction as denoted by arrows $A_2$ in FIG. 11. The conductive adhesive material 26 of the electrodes 12, 14 is conductive in a direction substantially orthogonal to the plane of the electrode 12 as denoted by arrows $A_2$. Accordingly, the conductive adhesive material 26 is conductive in the Z-axis direction. In addition, the conductive adhesive material 26 is also semi-conductive in a direction substantially laterally along the plane of the electrodes 12, 14 as denoted by arrows $A_3$. Accordingly, the conductive adhesive material 26 is semi-conductive in the X-Y directions.

Figure 12:
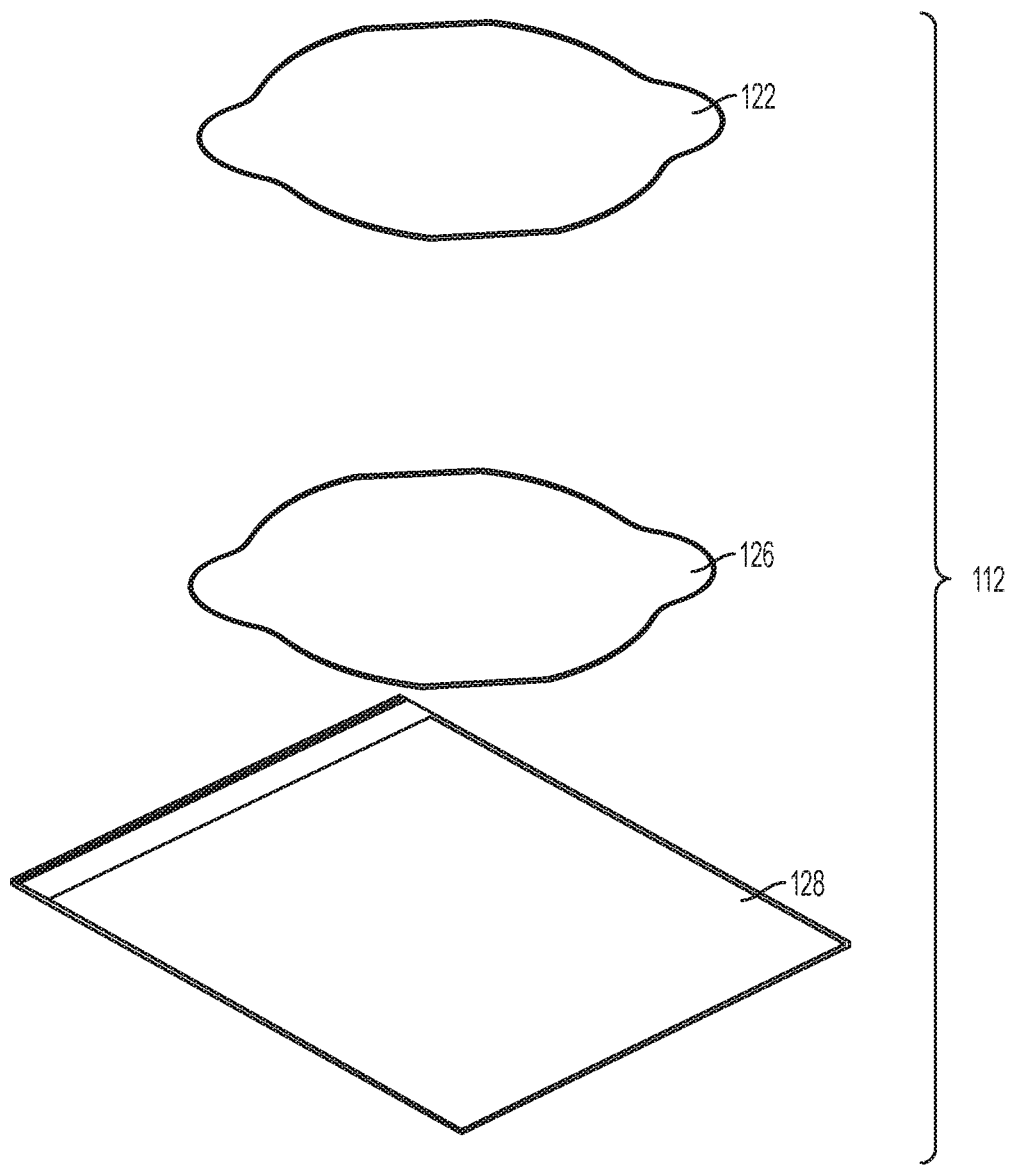
FIG. 12 is an expanded view of an electrode according to the present disclosure.

With reference to FIG. 12, another example of an electrode 112 comprises at least one non-conductive, flexible, water vapor-permeable, electrically insulating top layer 122 that provides, e.g., protection from short circuiting of the electrode against adjacent conductive objects in the vicinity of the patient during a defibrillation shock; a flexible, water vapor-permeable, conductive adhesive material 126 for contact with the patient's skin; and optionally a removable backing 128.

In this example, the conductive adhesive material 126 can comprise conductive particles distributed in a polymer material to provide conductive paths. Accordingly, the conductive adhesive material 126 can be manufactured from any of the materials described hereinabove with reference to conductive adhesive material 26.

In addition, the top layer 122 can be generally non-conductive, flexible, water vapor-permeable, electrically-insulating, and optionally at least substantially liquid-impermeable or waterproof. The non-conductive flexible, water-vapor permeable, electrically-insulating top layer 122 may comprise or consist of polyurethane, such as Tegaderm™ polyurethane film (available from 3M), Opsite™ polyurethane film (available from Smith & Nephew), or Hydrofilm™ polyurethane film (available from Hartman USA). The top layer 122 can provide some protection from defibrillation current inadvertently shocking someone close to the patient. In addition, where the top layer 122 is waterproof, the extended-wear electrodes disclosed herein may be worn when the user is showering.

Figure 13:
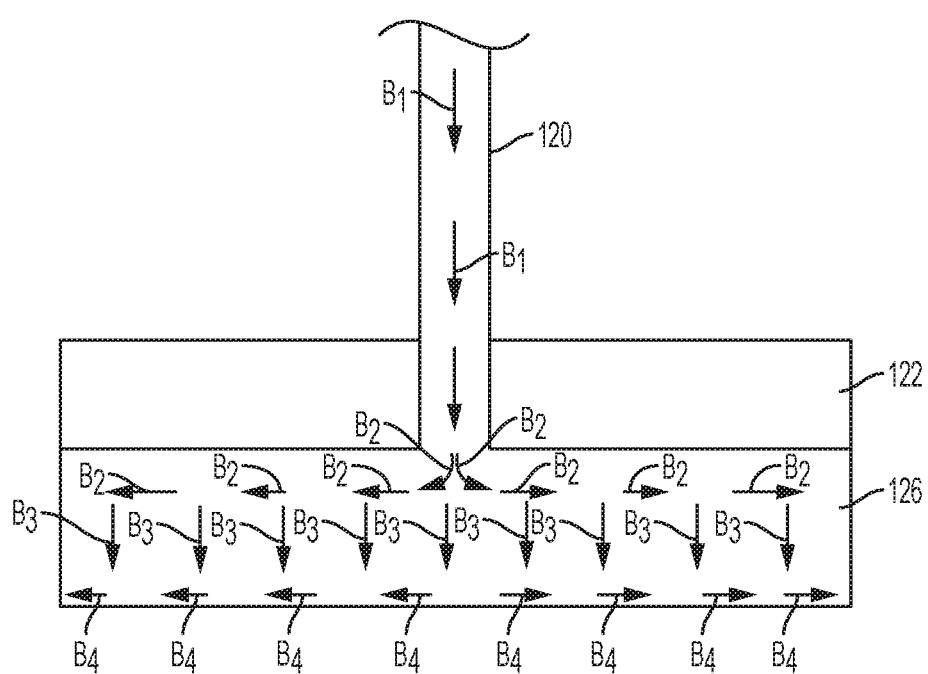
FIG. 13 is a schematic cross-sectional view of the electrode of FIG. 12.

With reference to FIG. 13, for example, the conductive adhesive material 126 is configured to substantially distribute a therapeutic current from a therapeutic current delivery device (not shown) over the plane of the electrode 112 prior to delivery to a subject. Current from a cable connector 120 connected between the therapeutic current delivery device and the conductive adhesive material 126 is provided, the conductive adhesive material 126 as denoted by arrows $B_1$. Since the conductive adhesive material 126 includes a plurality of conductive particles distributed in a polymer material, the conductive adhesive material 126 is conductive in both lateral (denoted by arrows $B_2$ and $B_4$) and orthogonal directions (denoted by arrows $B_3$) to a plane of the electrode. For example, the conductive adhesive material 126 can be configured by, e.g., controlling both its thickness and a density and shape of the conductive particles that are dispersed in the adhesive polymer matrix, to provide conductive paths in both the lateral and orthogonal directions relative to the plane of the electrode. In some examples, the conductive adhesive layer can be applied as a coating to the electrically-insulating top layer. Accordingly, the current distribution is uniform, thus preventing burning of the patient's skin as a result of therapeutic current delivery that is uneven across the face of the electrode and causing electrical current burns on the patient. In some implementations, a current dispersing element disposed in a similar manner as described in connection with FIG. 11 can also be included to improve current dispersing qualities of the electrode.

Electrodes in accordance with the present disclosure may include additional features not illustrated, for example, adhesive layers bonding the various components of the electrode together, labeling, a mechanism for holding the electrical conductor in place and in electrical contact with the conductive element, and/or packaging. Exemplary additional features are disclosed in U.S. patent application Ser. No. 13/079,336, titled BIOMEDICAL ELECTRODE, the disclosure of which is incorporated by reference herein in its entirety. Components of electrodes in accordance with examples of the present disclosure may be formed from materials having certain desirable properties. For example, an electrode may be formed of materials that render it radiolucent or radiotransparent, as disclosed in co-pending U.S. patent application Ser. No. 13/079,336. Further, electrodes in accordance with the present disclosure may communicate wirelessly with other circuitry.

Electrodes in accordance with the present disclosure may be substantially flat. For example, the electrodes may have a flat profile that is not noticeable or is minimally noticeable when attached to the subject, under the subject's clothes. The electrodes may also be substantially flexible. For example, the electrodes may conform to the contours of the subject's body during initial attachment to the subject, and may conform to body positioning changes when the subject is in motion. The electrodes can also be substantially devoid of rigid components, such as hard snaps, connectors, and rigid plates. For example, the electrodes may be devoid of hard rigid substances that may cause uncomfortable pressure points when a subject with the electrodes attached to his/her body is in a prone, prostrate, supine, or lateral position with the electrodes pressed against an object, such as a bed, couch, medical examining table, clothes, or medical equipment.

As shown in FIG. 1, the cable harness 18, which is connected to the defibrillator/monitor 16, includes three sensing element wires, two current dispersing element wires, and two ground wires. Two sensing element wires, one current dispersing element wire, and one ground wire are contained in an apex composite cable 44 of the cable harness 18 having an apex connector 46 for connecting the apex composite cable 44 to the apex electrode cable connector 20a, and one sensing element wire, one current dispersing element wire, and one ground wire are contained in an anterior composite cable 48 of the cable harness 18 having an anterior connector 50 for connecting the anterior composite cable 48 to the anterior electrode cable connector 20b. The apex electrode cable connector 20a includes a connector 52 adapted for connection to the apex connector 46 of the apex composite cable 44 and three individual wires 32 each having a connector, such as a snap or an alligator clip, for connecting to the electrical connectors 38 of the apex electrode 12, and the anterior electrode cable connector 20b includes a connector 56 for connection to the anterior connector 50 of the anterior composite cable 48 and two individual wires 34 each having a connector for connecting to the electrical connectors 38 of the anterior electrode 14. The connectors 46, 50 of the cable harness 18 and the connectors 52, 56 of the apex electrode cable connector 20a and the anterior electrode cable connector 20b may have structures, markings, colors, and the like so that it is clear which connector 46, 50 of the cable harness 18 is to be connected to the apex electrode cable connector 20a and which connector 46, 50 of the cable harness 18 is to be connected to the anterior electrode cable connector 20b and may further include structure that only allows the proper connection to be made.

The individual wires 32, 34 of the apex electrode cable connector 20a and the anterior electrode cable connector 20b may alternatively be hard wired to the electrical connectors 38 of the electrodes 12, 14.

The length of the apex electrode cable connector 20a and the anterior electrode cable connector 20b should be minimized, especially when they are hardwired to the electrodes 12, 14, so that they provide as little force on the thin flexible electrodes 12, 14 during placement on the patient's skin as possible. For example, the apex electrode cable connector 20a and the anterior electrode cable connector 20b should have a maximum length no longer than 10 inches and preferably, no longer than 9 inches.

Although the disclosure has been described in detail for the purpose of illustration based on what is currently considered to be the most practical and preferred examples, it is to be understood that such detail is solely for that purpose and that the disclosure is not limited to the disclosed examples but, on the contrary, is intended to cover modifications and equivalent arrangements that are within the spirit and scope of the appended claims. For example, it is to be understood that the present disclosure contemplates that, to the extent possible, one or more features of any example can be combined with one or more features of any other example.

The disclosure claimed is:

1. An electrode for use with a therapeutic current delivery system, comprising:
    a flexible, water vapor-permeable, conductive adhesive material;
    a current dispersing element in contact with the conductive adhesive material; and
    a non-conductive, flexible, water vapor-permeable, electrically-insulating top layer provided in contact with the current dispersing element;
    wherein the current dispersing element is conductive at least laterally along a plane of the electrode; and
    wherein the conductive adhesive material is conductive in a direction substantially orthogonal to the plane of the electrode and semi-conductive in a direction substantially lateral to the plane of the electrode.

2. The electrode of claim 1, wherein the current dispersing element is conductive in a direction orthogonal to the plane of the electrode.

3. The electrode of claim 1, wherein the water vapor permeability of the electrode is greater than 100 gm/m$^2$/24 hours.

4. The electrode of claim 1, wherein the therapeutic current delivery system is a defibrillation system.

5. The electrode of claim 1, wherein the therapeutic current delivery system is a pacing system.

6. The electrode of claim 1, wherein the electrode is configured to deliver a defibrillation pulse.

7. The electrode of claim 6, wherein the defibrillation pulse comprises a therapeutic pulse having an energy of at least 200 joules.

8. The electrode of claim 1, wherein the electrode is configured to deliver at least one pacing pulse.

9. The electrode of claim 8, wherein the pacing pulse comprises a current pulse having a duration in a range of 10-40 ms and an amplitude of at least 50 mAmps.

10. The electrode of claim 1, wherein the electrode is configured to uniformly distribute current to a patient.

11. The electrode of claim 1, wherein the flexible, water vapor-permeable, conductive adhesive material comprises a material selected from the group consisting of an electrospun polyurethane adhesive, a polymerized microemulsion pressure sensitive adhesive, an organic conductive polymer, an organic semi-conductive conductive polymer, an organic conductive compound and a semi-conductive conductive compound, and combinations thereof.

12. The electrode of claim 1, wherein the flexible, water vapor-permeable, conductive adhesive layer comprises a material selected from the group consisting of poly(3,4-ethylene dioxitiophene), doped with poly(styrene sulfonate), (PEDOT:PSS) poly(aniline) (PANI), poly(thiopene)s, and poly(9,9-dioctylfluorene co-bithiophen) (F8T2), and combinations thereof.

13. The electrode of claim 1, wherein a thickness of the flexible, water vapor-permeable, conductive adhesive material is between 0.25 and 50 mils.

14. The electrode of claim 1, wherein the flexible, water vapor-permeable, conductive adhesive material comprises conductive particles.

15. The electrode of claim 1, wherein the current dispersing element comprises a metallic wire mesh.

16. The electrode of claim 15, wherein the metallic wire mesh comprises a metal selected from the group consisting of copper, tin, nickel, silver, gold, and combinations thereof.

17. The electrode of claim 1, wherein the conductive, current dispersing element comprises nickel-plated carbon-filled fibers.

18. The electrode of claim 1, wherein the current dispersing element is segmented.

19. The electrode of claim 1, further comprising a backing attached to the flexible, water vapor-permeable, conductive adhesive material.

20. The electrode of claim 19, wherein the backing extends beyond an outer surface of the electrode.

21. The electrode of claim 1, further comprising a frame provided on an outer surface of the non-conductive, flexible, water vapor-permeable, electrically-insulating top layer.

22. The electrode of claim 21, wherein the frame is disposed around the perimeter of the electrode.

23. A therapeutic current delivery system comprising:
a therapeutic current delivery device;
at least one cable connector connected to the therapeutic current delivery device; and
at least one electrode connected to the at least one cable connector,
wherein the at least one electrode comprises:
a flexible, water vapor-permeable, conductive adhesive material;
a current dispersing element in contact with the conductive adhesive material; and
a non-conductive, flexible, water vapor-permeable, electrically-insulating top layer provided in contact with the current dispersing element;
wherein the current dispersing element is conductive at least laterally along a plane of the electrode; and
wherein the conductive adhesive material is conductive in a direction substantially orthogonal to the plane of the electrode and semi-conductive in a direction substantially lateral to the plane of the electrode.

24. The system of claim 23, wherein the cable connectors are no more than 10 inches long.

25. The system of claim 23, wherein the therapeutic current delivery device is a defibrillation device.

26. The system of claim 23, wherein the therapeutic current delivery device is a pacing device.

27. The system of claim 23, wherein the therapeutic current delivery device is a nerve stimulation device.

28. An electrode for use with a therapeutic current delivery system, comprising:
a flexible, water vapor-permeable, conductive adhesive material;
a current dispersing element in contact with the conductive adhesive material to receive a therapeutic current from a connector and distribute the therapeutic current over a plane of the electrode; and
a non-conductive, flexible, water vapor-permeable, electrically-insulating top layer in contact with the current dispersing element;
wherein the conductive adhesive material is conductive in a direction substantially orthogonal to a plane of the electrode and semi-conductive in a direction substantially lateral to the plane of the electrode.

29. The electrode of claim 28, wherein the water vapor permeability of the electrode is greater than 100 gm/m²/24 hours.

30. An electrode for use with a therapeutic current delivery system, comprising:
a non-conductive, flexible, water vapor-permeable, electrically-insulating top layer; and
a flexible, water vapor-permeable, conductive adhesive material disposed on one side of the electrically-insulating top layer, wherein the conductive adhesive material configured to provide conductive paths in both lateral and orthogonal directions to a plane of the electrode,
wherein the electrode is configured to deliver a defibrillation pulse comprising a therapeutic pulse having an energy of at least 200 joules.

31. The electrode of claim 30, wherein the top layer is in contact with the conductive adhesive material.

32. An electrode for use with a therapeutic current delivery system, comprising:
a non-conductive, flexible, water vapor-permeable, electrically-insulating top layer; and
a flexible, water vapor-permeable, conductive adhesive material disposed on one side of the electrically-insulating top layer, wherein the conductive adhesive material configured to provide conductive paths in both lateral and orthogonal directions to a plane of the electrode,
wherein the electrode is configured to deliver at least one pacing pulse comprising a current pulse having a duration in a range of 10-40 ms and an amplitude of at least 50 mAmps.

33. An electrode for use with a therapeutic current delivery system, comprising:
a non-conductive, flexible, water vapor-permeable, electrically-insulating top layer; and
a flexible, water vapor-permeable, conductive adhesive material disposed on one side of the electrically-insulating top layer, wherein the conductive adhesive material configured to provide conductive paths in both lateral and orthogonal directions to a plane of the electrode,
wherein the conductive adhesive material comprises conductive particles distributed in a polymer material to provide the conductive paths.

34. An electrode for use with a therapeutic current delivery system, comprising:
a non-conductive, flexible, water vapor-permeable, electrically-insulating top layer; and
a flexible, water vapor-permeable, conductive adhesive material disposed on one side of the electrically-insulating top layer, wherein the conductive adhesive material configured to provide conductive paths in both lateral and orthogonal directions to a plane of the electrode,
wherein the conductive adhesive material is configured to substantially distribute a therapeutic current over the plane of the electrode prior to delivery to a subject.

35. An electrode for use with a therapeutic current delivery system, comprising:
a non-conductive, flexible, water vapor-permeable, electrically-insulating top layer;
a flexible, water vapor-permeable, conductive adhesive material disposed on one side of the electrically-insulating top layer, wherein the conductive adhesive material configured to provide conductive paths in both lateral and orthogonal directions to a plane of the electrode; and
a current dispersing element in contact with the conductive adhesive material and configured to be conductive at least laterally along the plane of the electrode.

36. An electrode for use with a therapeutic current delivery system, comprising:
a non-conductive, flexible, water vapor-permeable, electrically-insulating top layer; and
a flexible, water vapor-permeable, conductive adhesive material disposed on one side of the electrically-insulating top layer, wherein the conductive adhesive material configured to provide conductive paths in both lateral and orthogonal directions to a plane of the electrode,
wherein the water vapor permeability of the electrode is greater than 100 gm/m²/24 hours.

* * * * *

UNITED STATES PATENT AND TRADEMARK OFFICE
CERTIFICATE OF CORRECTION

PATENT NO. : 9,867,976 B2  
APPLICATION NO. : 15/060694  
DATED : January 16, 2018  
INVENTOR(S) : Gary A. Freeman Page 1 of 1

It is certified that error appears in the above-identified patent and that said Letters Patent is hereby corrected as shown below:

In the Claims

Column 18, Line 38, Claim 12, delete "dioxitiophene)," and insert -- dioxythiophene), --

Column 18, Line 39, Claim 12, delete "poly(thiopene)s," and insert -- poly(thiophene)s, --

Column 18, Line 40, Claim 12, delete "co-bithiophen)" and insert -- co-bithiophene) --

Signed and Sealed this  
Eighth Day of May, 2018

Andrei Iancu  
*Director of the United States Patent and Trademark Office*